US00PP31055P3

(12) United States Plant Patent

Klemm et al.

(10) Patent No.: US PP31,055 P3
(45) Date of Patent: Nov. 12, 2019

(54) *PELARGONIUM* PLANT NAMED 'KLEPZ17434'

(50) Latin Name: *Pelargonium zonale*
Varietal Denomination: KLEPZ17434

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/932,696

(22) Filed: Apr. 10, 2018

(65) Prior Publication Data

US 2019/0313564 P1 Oct. 10, 2019

(51) Int. Cl.
*A01H 5/02* (2018.01)
*A01H 6/42* (2018.01)

(52) U.S. Cl.
USPC ..... Plt./327
CPC ..... *A01H 6/425* (2018.05)

(58) Field of Classification Search
USPC ..... Plt./327
CPC ..... A01H 6/42
See application file for complete search history.

*Primary Examiner* — Keith O. Robinson
(74) *Attorney, Agent, or Firm* — Barbara Campbell; Cochran Freund & Young LLC

(57) ABSTRACT

A new *pelargonium* plant particularly distinguished by large, salmon-colored flowers with a lighter border and strong zonation of the leaves, is disclosed.

1 Drawing Sheet

Genus and species: *Pelargonium zonale.*
Variety denomination: 'KLEPZ17434'.

CROSS-REFERENCE TO RELATED APPLICATIONS

A Switzerland Plant Breeders Rights application was filed on May 24, 2017, Application No. 17-3145, and an European Community Plant Variety Office application was filed on May 31, 2017, File No. 2017-1444. 'KLEPZ17434' has not been sold or made publicly available more than one year prior to the filing date of the instant application.

BACKGROUND OF THE NEW PLANT

The present invention comprises a new and distinct variety of *pelargonium*, botanically known as *Pelargonium zonale* and hereinafter referred to by the variety name 'KLEPZ17434'. 'KLEPZ17434' originated from a cross-pollination in August 2011 in Stuttgart, Germany between the female *pelargonium* variety 'SIL Gattwig' (unpatented) and the proprietary male *pelargonium* variety 'KLEP04134' (U.S. Plant Pat. No. 18,021).

Seeds from the cross-pollination were obtained. The seeds were sown and plants were grown for evaluation. A single plant was selected in June 2012 and subsequently named 'KLEPZ17434'. In August 2012 'KLEPZ17434' was first vegetatively propagated by vegetative stem cuttings. 'KLEPZ17434' was found to reproduce true to type in successive generations of asexual propagation via vegetative stem cuttings in Stuttgart, Germany.

SUMMARY

The following are the most outstanding and distinguishing characteristics of this new variety when grown under normal horticultural practices in Stuttgart, Germany.

1. Large, salmon-colored flowers with a lighter border; and
2. Strong zonation of the leaves.

DESCRIPTION OF THE PHOTOGRAPH

This new *pelargonium* plant is illustrated by the accompanying photograph which shows an overall view of the plant. The photograph is of an approximately 8 to 9-week-old plant grown in Stuttgart, Germany under greenhouse conditions in May 2015. The colors shown are as true as can be reasonably obtained by conventional photographic procedures.

DESCRIPTION OF THE NEW VARIETY

The following detailed descriptions set forth the distinctive characteristics of 'KLEPZ17434'. The data which define these characteristics were collected from asexual reproductions carried out in Stuttgart, Germany. Data was collected on 3-month-old plants in Stuttgart, Germany under greenhouse conditions in April 2017. Color references are to The R.H.S. Colour Chart of The Royal Horticultural Society of London (R.H.S.), $5^{th}$ edition (2007).

Classification:
*Family.*—Geraniaceae.
*Botanical.*—*Pelargonium zonale.*
*Common.*—*Pelargonium.*
*Designation.*—'KLEPZ17434'.

Parentage:
*Female parent.*—The female *pelargonium* variety 'SIL Gattwig' (unpatented).
*Male parent.*—The proprietary male *pelargonium* variety 'KLEP04134' (U.S. Plant Pat. No. 18,021).

Plant:
*Form.*—Round.
*Habit.*—Upright.
*Height.*—16.0 cm.
*Spread.*—20.0 cm.
*Natural flowering season.*—Spring to autumn.
*Propagation type.*—Vegetative stem cuttings.
*Time to produce a finished flowering plant.*—4 months.
*Time to initiate and develop roots.*—20 days.
*Root description.*—Fine and white, and RHS NN155C.

Stems:
*Quantity of stems per plant.*—4 to 5.
*Color.*—RHS 137D.
*Surface texture.*—Sparsely pubescent.
*Stem form.*—Round.
*Diameter.*—0.9 cm.
*Length.*—6.0 cm to 8.0 cm.
*Internode length.*—1.5 cm to 2.0 cm.
*Anthocyanin.*—Absent.

Leaves:
*Arrangement.*—Alternate.
*Shape.*—Kidney-shaped.
*Apex.*—Round.
*Base.*—Slightly open.
*Margin.*—Crenate.
*Surface texture.*—Upper surface: Sparsely pubescent. Lower surface: Sparsely pubescent.
*Length.*—6.0 cm to 8.0 cm.
*Width.*—6.0 cm to 8.0 cm.
*Color.*—Upper surface: RHS 137A and RHS 183B. Lower surface: RHS 137C.
*Petiole.*—Length: 5.0 cm. Diameter: 0.2 cm. Color: RHS 137B. Strength: Medium.
*Venation pattern.*—Palmate.
*Venation color.*—Upper surface: RHS 137A. Lower surface: RHS 138C.
*Variegation.*—Absent.

Inflorescence:
*Lastingness of flowers on the plant.*—6 to 8 days.
*Umbels.*—Quantity of umbels per plant: 2 to 3. Length: 6.0 cm. Diameter: 12.0 cm.
*Individual florets of the umbel.*—Quantity of florets per umbel: 35 to 40. Depth: 2.0 cm. Diameter: 5.0 cm.
*Flower type.*—Semi-double.
*Fragrance.*—Absent.

Flower buds:
*Cluster shape.*—Elliptic to round.
*Cluster size.*—Length: 3.0 cm. Width: 4.0 cm.
*Surface texture.*—Sparsely pubescent.
*Bud.*—Height: 1.0 cm. Width: 0.8 cm. Shape: Elliptic. Apex: Acute. Base: Obtuse. Margin: Entire. Color: RHS 138B.

Petals:
*Quantity per flower.*—5 to 7.
*Shape.*—Spatulate.
*Apex.*—Round.
*Base.*—Obtuse.
*Margin.*—Entire.
*Length.*—2.5 cm.
*Width.*—2.5 cm.
*Surface texture.*—Upper surface: Smooth. Lower surface: Smooth.
*Color of lobes.*—Upper lobes: Upper surface: RHS 41C and RHS 49D. Lower surface: RHS 41D and RHS 49D. Lower lobes: Upper surface: RHS 41C and RHS 49D. Lower surface: RHS 41C and RHS 49D.

Petaloids:
*Quantity per flower.*—1 to 4.
*Shape.*—Moderate.
*Apex.*—Acute.
*Base.*—Obtuse.
*Margin.*—Entire.
*Texture (upper and lower surfaces).*—Smooth.
*Length.*—0.2 cm to 1.0 cm.
*Width.*—0.1 cm to 0.5 cm.
*Color.*—Upper surface: RHS 41C. Lower surface: RHS 49D.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Sparsely pubescent.
*Color.*—Upper surface: RHS 137D. Lower surface: RHS 137D.
*Length.*—0.8 cm.
*Width.*—0.4 cm.

Pedicel:
*Length.*—4.0 cm to 5.0 cm.
*Diameter.*—0.2 cm.
*Color.*—RHS 166D.
*Surface texture.*—Sparsely pubescent.
*Strength.*—Medium.

Peduncle:
*Length.*—8.0 cm to 12.0 cm.
*Diameter.*—0.7 cm.
*Color.*—RHS 138A.
*Surface texture.*—Sparsely pubescent.
*Strength.*—Medium to strong.

Reproductive organs:
*Stamens.*—Quantity of stamens per flower: Moderate, 5. Anther length: 0.2 cm. Filament length: 0.8 cm. Filament color: RHS 73D. Pollen amount: Moderate. Pollen color: RHS 29A.
*Pistils.*—Number: 1. Stigma color: RHS 42D. Style length: 0.6 cm. Style color: RHS 36B. Ovary arrangement: Central. Ovary color: RHS 138D. Ovary diameter: 0.2 cm. Ovary length: 0.1 cm.

Fruit and seed set: None observed.
Disease and pest/insect resistance: None observed.

COMPARISON WITH PARENTAL LINES AND KNOWN VARIETY

'KLEPZ17434' is distinguished from its parents as described in Table 1:

TABLE 1

Comparison with Parental Lines

| Characteristic | 'KLEPZ17434' | Female parent 'SIL Gattwig' | Male Parent 'KLEP04134' |
|---|---|---|---|
| Flower color | Salmon with a lighter border | Dark salmon with a lighter border | Dark salmon |

TABLE 1-continued

| Comparison with Parental Lines | | | |
|---|---|---|---|
| Characteristic | 'KLEPZ17434' | Female parent 'SIL Gattwig' | Male Parent 'KLEP04134' |
| Growth | Medium | Medium-strong | Strong |
| Leaf zonation | Strong | Medium | Light |

'KLEPZ17434' can be compared to the commercial variety 'Sunrise Rosetta' (unpatented). Differences between the two varieties are described in Table 2:

TABLE 2

| Comparison with Similar Variety | | |
|---|---|---|
| Characteristic | 'KLEPZ17434' | Commercial line 'Sunrise Rosetta' |
| Flower color | Salmon with a lighter border | Dark salmon with a lighter border |
| Flower size | Large | Medium |
| Growth | Medium | Compact |

We claim:

1. A new and distinct variety of *pelargonium* plant named 'KLEPZ17434' as illustrated and described herein.

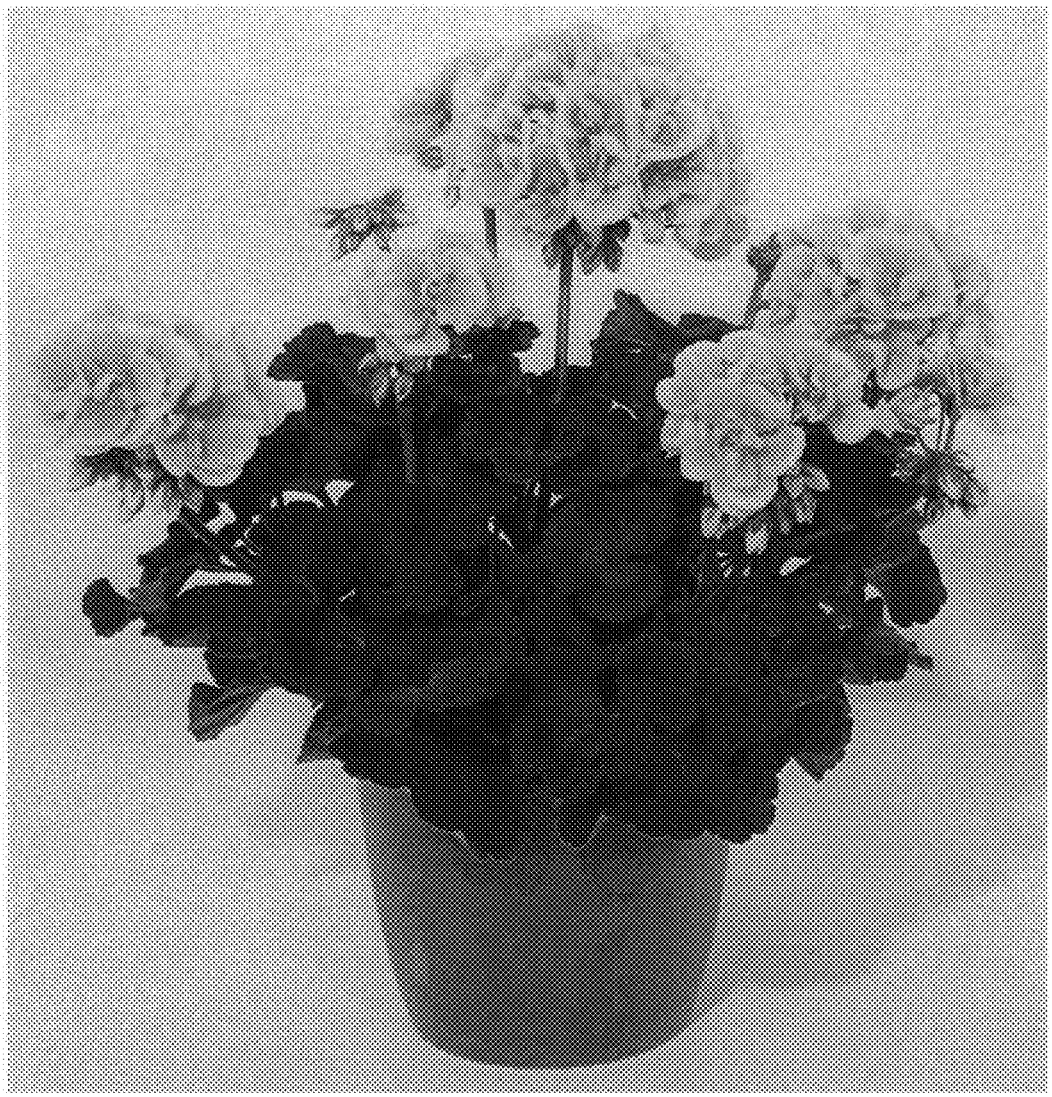

* * * * *